US005562735A

United States Patent [19]

Margulies

[11] Patent Number: 5,562,735
[45] Date of Patent: Oct. 8, 1996

[54] SPINAL STABILIZATION SYSTEM AND IMPROVED METHOD

[75] Inventor: Joseph Y. Margulies, New York, N.Y.

[73] Assignee: Hospital for Joint Diseases, New York, N.Y.

[21] Appl. No.: 145,603

[22] Filed: Nov. 4, 1993

Related U.S. Application Data

[63] Continuation-in-part of Ser. No. 973,294, Nov. 9, 1992, abandoned.

[51] Int. Cl.⁶ ........................................ A61F 2/10
[52] U.S. Cl. ................................. 623/17; 606/61
[58] Field of Search .................. 623/17, 18; 606/61, 606/54, 57, 64, 71

[56] References Cited

U.S. PATENT DOCUMENTS 3,900,025  8/1975  Barnes, Jr. .......................... 606/71
4,456,005  6/1984  Lichty ............................. 606/61 X
4,913,134  4/1990  Luque ............................. 606/61 X

FOREIGN PATENT DOCUMENTS 829104   5/1981   U.S.S.R. ............................. 606/61
1771717  10/1992  U.S.S.R. ............................. 606/61

Primary Examiner—Michael J. Milano
Attorney, Agent, or Firm—Stephen E. Feldman

[57] ABSTRACT

A spinal stabilization system for fixing affected vertebrae having anterior and posterior aspects. The system comprises a plurality of rods or plates disposed over the affected vertebrae, at least one rod or plate disposed anteriorly and at least one disposed posteriorly, and a plurality of bolts and nuts extending laterally through the affected vertebrae and attached to the rods.

16 Claims, 4 Drawing Sheets

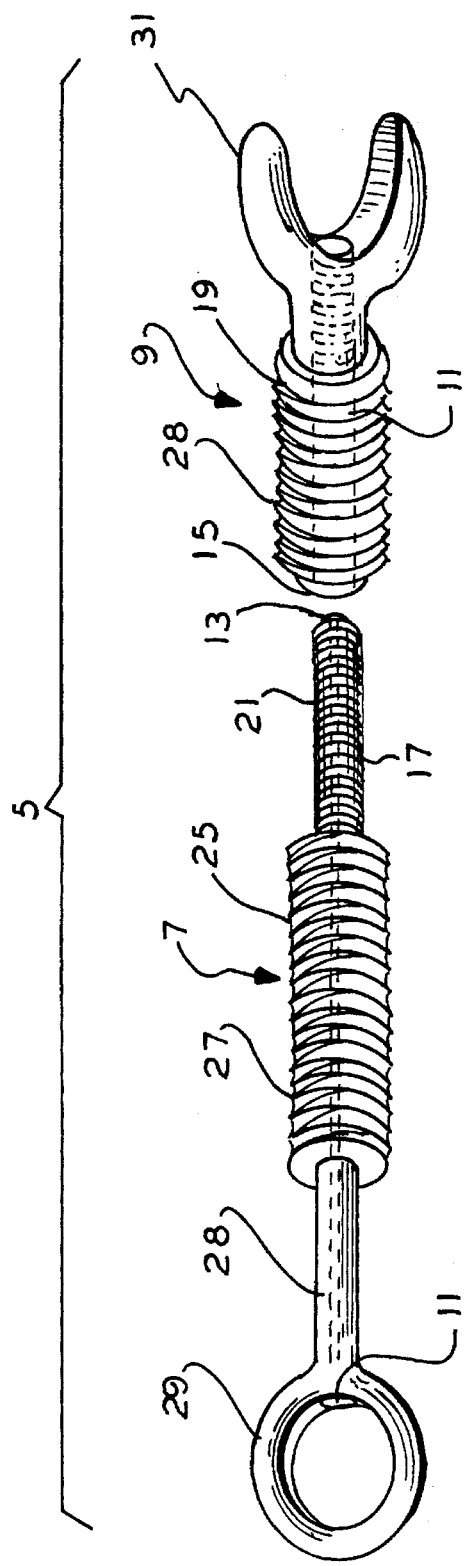
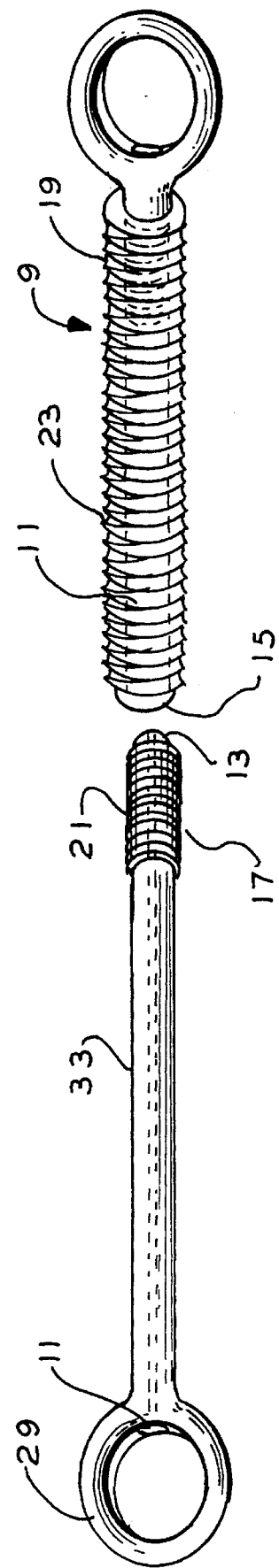
FIG. 4A
FIG. 4B

SPINAL STABILIZATION SYSTEM AND IMPROVED METHOD

FIELD OF THE INVENTION

This application is a continuation-in-part of application Ser. No. 07/973,294, filed Nov. 9, 1992 now abandoned.

This invention relates to a system of spinal stabilization, a method for fixing vertebrae and an alignment fixture used to install said system.

BACKGROUND OF THE INVENTION

Spinal stabilization is a common method to treat pathological processes in the spine and/or sacrum. Stabilization means eliminating movement between adjacent vertebrae, and therefore restoring structural integrity to the spine. Stabilization is achieved by fusing affected vertebrae to each other. The technical objective of stabilization is to achieve a solid bony fusion. This is usually done by creating a "fracture situation" between adjacent affected vertebrae, and fixating them mechanically with metal implants. Once fixation is accomplished, bone healing occurs, creating a fusion mass, which replaces the spanned vertebrae with one solid piece of bone. The task of the implanted instrumentation is to hold fractured or injured bone surfaces rigidly together until healing and fusion occur.

Without bone fusion the stability of a mechanical construct is inadequate. The present surgical state of the art is a circumferential (anterior and posterior) approach, to rebuild the anterior and the posterior mechanical segments of the spinal column separately.

The disadvantages of the circumferential approach are several: too much metal in two different sets of devices; the construct may fail to promote stress sharing and may create stress shielding; and the construct may be too strong for osteogenic bone, and thus cut through it.

A major problem of the present day approach is what to do with poor quality bone or with spines in which adequate attachment of the construct to the bone cannot be achieved.

SUMMARY OF THE INVENTION

The present invention in its broadest aspect provides a single spinal stabilization system for fixing affected vertebrae having anterior and posterior aspects. The system comprises a plurality of substantially rigid, elongated column means disposed over the affected vertebrae. At least one of the column means is disposed over the anterior aspect of the affected vertebrae. At least another of the column means is disposed over the posterior aspect of the affected vertebrae. A plurality of substantially rigid, elongated beam means which extend through these affected vertebrae are attached to the column means.

Additionally, the present invention in one of its broadest aspects provides a method of installing a spinal stabilization system to fix affected vertebrae. The steps comprise exposing the spine anteriorly and posteriorly at the level of the affected vertebra, inserting one or a pair of beam means through the affected vertebra, repeating the exposing and inserting steps for a next level of vertebra, disposing column means over the anterior and posterior aspects of the two levels of affected vertebrae, and connecting the ends of the beam means at each affected vertebra level to said column means.

Another feature of the present invention in its broadest aspect is to provide an alignment fixture which accurately place the elements of the spinal stabilization system. The alignment fixture comprises a first and second arm, each arm having first and second ends, a drill guide means and an aiming pin. The arm pin and drill guide means are fixedly connected to the first end of said first and second arms, respectively. The second ends of said first and second arms are connected in sliding engagement with one another. The first and second arms, the drill guide means and the aiming pin are all disposed in the same plane.

Furthermore, the present invention in still another of its broadest aspects, provides a method of installing a spinal stabilization system to fix the vertebrae of a patient using the aligning fixture which has a drill guide at one end and an aiming pin at the other end. This method comprises the steps of:

a. surgically exposing two adjacent levels of affected vertebrae anteriorly and posteriorly;

b. cleaning out the contents of the pedicle portions of the adjacent levels of affected vertebrae so as to permit sufficient movement of the drill guide within the cleaned cut pedicle portions so that the aiming pin can be positioned at the desired exit points on the anterior aspect of the adjacent levels of affected vertebrae;

c. inserting the drill guide within the cleaned out pedicle portions of the adjacent levels of affected vertebrae;

d. positioning the aiming pin at the desired exit points on the anterior aspect of the adjacent levels of affected vertebrae;

inserting a drilling means within the aligned drill guide disposed within the pedicle portions of the adjacent levels of affected vertebrae; and f. drilling holes through the aligned drill guide into the affected vertebrae to the desired exit points.

The principal object of the invention is to create a rigid structure that will allow successful bony fusion by using a new concept combining anterior and posterior constructs into a single unitary structure achieved at a single surgical sitting.

Another object of the invention is to provide a more rigid construct or cage in which bone and bone graft can heal to a solid fusion.

A further object of the invention is to provide an improved solid construct, in which stress sharing is better distributed between anterior and posterior elements.

An additional object of the invention is to provide an improved method and an alignment fixture for installing such construct or cage.

BRIEF DESCRIPTION OF THE DRAWINGS

FIG. 4A is a perspective view of a preferred embodiment of a single unassembled bolt and nut portions of the present invention;

FIG. 4B is a perspective view of a preferred embodiment of another single unassembled bolt and nut portions of the present invention for use with smaller vertebrae;

DESCRIPTION OF THE INVENTION

Figure 3:
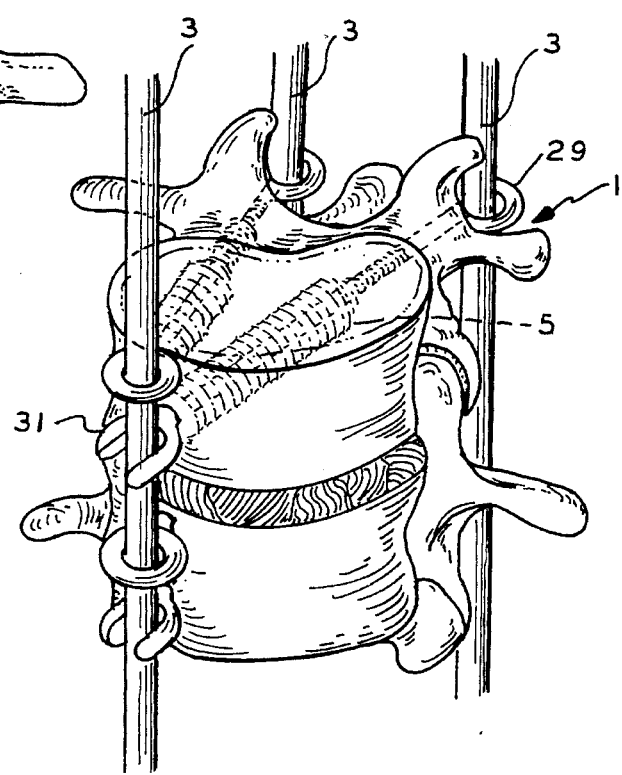
FIG. 3 is a perspective view of the implanted spinal stabilization system of the present invention.

The preferred embodiment of the spinal stabilization or fixation system for treating pathological processes or fixing affected vertebrae having anterior and posterior aspects is generally designated by the reference character 1 and its complete assembly is shown in FIG. 3. An example of a pathological process in the spine having affected vertebrae is the common prolapsed invertebral disc; the vertebrae adjacent said disc are the affected vertebrae. The system comprises conventional, column means 3, three in number, each of which is a rigid elongated rod or plate, one of which is disposed over the anterior aspect of at least two such affected vertebrae, and as shown in this figure two vertebrae, and two of which rods are disposed over the posterior aspects of the two vertebrae. These rods 3 are attached to beam means 5, four in number, each of which is a rigid elongated beam means which extends through individual vertebrae. It should be noted however that two or three or more rods could be used. Referring specifically to FIG. 4A, which illustrates in detail a single beam means 5 which comprises a pedicle bolt section 7 and a nut section 9, each of which sections are adapted to join each other when they are inserted through a vertebra when the system 1 is installed. Each of these bolt and nut sections 7 and 9, respectively, preferably have an aperture or cannulation 11 extending along the longitudinal axes thereof; such cannulation 11 is however optional. Each of the bolt and nut sections 7 and 9, respectively, have a cutting end portion 13 and 15, and a front portion 17 and 19, having a cylindrical periphery 21 and 23, respectively, which is externally threaded with cutting edges. The aperture 11 of the nut section 9 has a cylindrical periphery which is internally threaded for receiving and engaging the threads on the front portion 17 of the bolt section 7. The bolt section 7 also comprises a middle portion 25 having a cylindrical periphery 27 which is externally threaded with cutting edges; equal diameters are used for the middle and front portions 25 and 19, respectively. The middle portion 25 is connected to a smooth shaft portion 28. Each of the bolt and nut sections 7 and 9, respectively, have a rear portion or ends 29 and 31, respectively, for attaching the ends of said nuts and bolts 7 and 9, respectively, to said rods 3, as is best shown in FIG. 3. These ends or attachments 29 and 31 are shown as closed and open attachments, respectively, in FIG. 4A, whereas one of said beam means 5 is shown having closed attachments at both ends; after the attachments are installed a staple or a plate (not shown) can be disposed beneath the attachments.

Another preferred embodiment of the beam means 5 is shown in FIG. 4B and is utilized when the system is used for fixing smaller vertebrae. Its middle portion 33 comprises a smooth shaft portion, the diameter of which is slightly less than the diameter of the threaded portion 21 of the front portion 17. Its attachments 29 and 31 are of the closed type.

Figure 6:
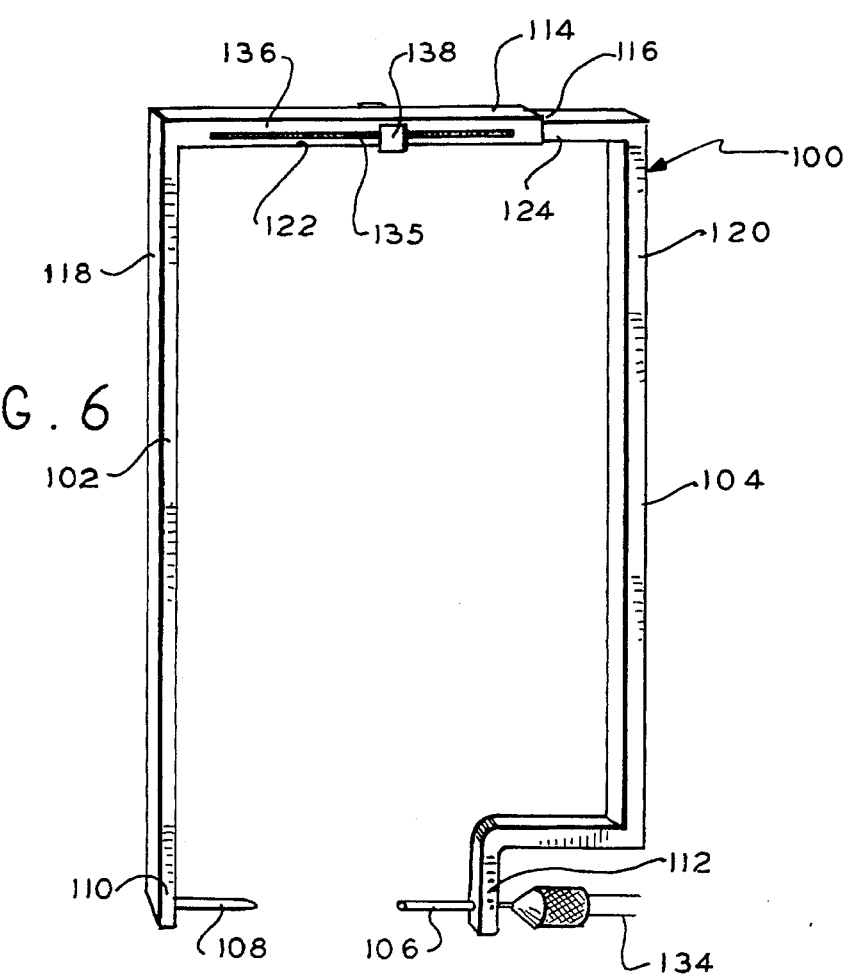
FIG. 6 is a perspective view of an alignment fixture used for installing the spinal stabilization system.

The preferred embodiment of the alignment fixture used for assisting in the installation of the previously described spinal stabilization system 1 is generally designated by the reference character 100 and its complete assembly is shown in FIG. 6. The alignment fixture 100 comprises L-shaped first and second arms 102 and 104, respectively, drill guide means 106 and an aiming pin 108, all of which are disposed in the same plane. Each of the first and second arms 102 and 104, respectively, have first and second ends 110, 112 and 114, 116, respectively. Additionally, each of the first and second arms 102 and 104, respectively, have first and second straight portions 118, 120 and 122, 124, respectively. The first portions 118 and 120 of the first and second arms 102 and 104, respectively, are disposed opposite one another as are their first ends 110 and 112. The second portion 122 is U-shaped in cross-section and has a narrow slot 135 extending across it length in side walls 136. A slide 138 extends through the slots 135 and is fixedly attached to the second end 116 of the second portion 124. Accordingly, the second portions 122 and 124 of the first and second arms 102 and 104, respectively, are connected in sliding engagement with one another as are their second ends 114 and 116. The aiming pin 108 and the drill guide means 106 are axially aligned and fixedly disposed orthogonally on the first ends 110 and 112 of the first portions 118 and 120, respectively, of the first and second arms 102 and 104, respectively. The aiming pin 108 is generally cylindrical along its length except that its inward end is conically shaped. The drill guide means 106 comprises a hollow tube which extends inward for most of its length and extends completely through the first end 112 of the second arm 104. As discussed below, the aiming pin 108 and the drill guide means 105 on the first and second arms 102 and 104, respectively, of the alignment fixture 100, will be utilized and disposed at the anterior and posterior aspects, respectively, of the vertebrae during the initial stages of the installation of the spinal stabilization system 1. Such positioning is accomplished by moving the slide 130 appropriately thereby moving the sliding arms 102 and 104 forward or backwards, until the aiming pin 108 and the drill guide 106 are properly disposed on the anterior and posterior aspects, respectively, of the vertebrae.

Figure 1:
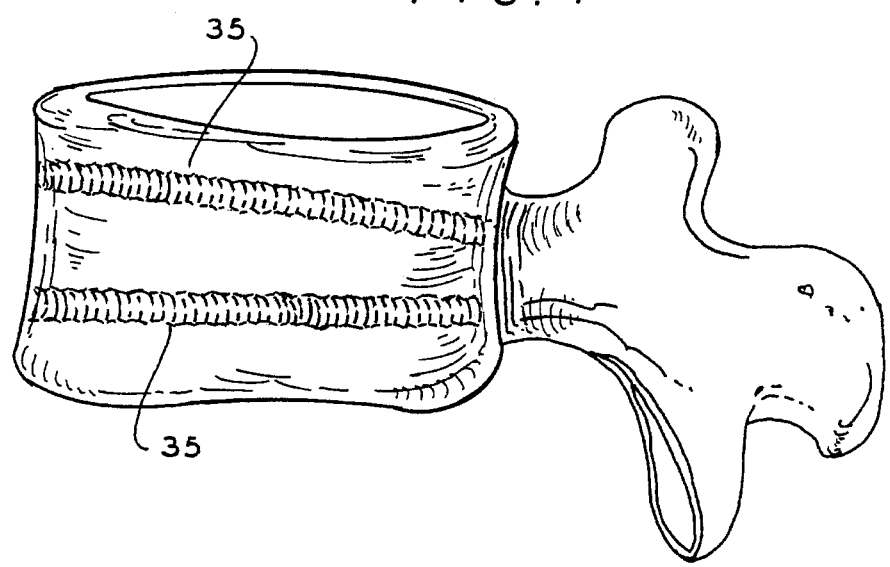
FIG. 1 is a perspective view of an individual vertebra showing the threaded apertures which are formed by insertion of a pair of nut and bolt portions of the present invention.

The surgical technique used for implanting the preferred system of the present invention without using the alignment fixture is generally described as follows (for fixing two levels of affected vertebrae). A portion of the spine is surgically exposed anteriorly and posteriorly simultaneously to reveal two levels of vertebrae. Then one or a pair of beam means 5 are inserted through an individual vertebra; more specifically one or two pedicle bolt sections 7 each shown as having a cannulation 11, are inserted from posterior to anterior through the vertebra so as to join its opposite bolt section 7; that is the cannulation 11 of each nut section 9 engages the threads on the front portion 17 of each bolt section 7. The route in the vertebrae (FIG. 1) can be prepared over a guide wire utilizing a cannula, which requires usage of cannulated bolt and nut sections. The above described procedure is then repeated for the next vertebral level and then three column means or rigid elongated rods 3 are disposed over the anterior and posterior aspects of the two vertebrae and connected to these rods 3. More specifically the rear portions or ends 29 and 31, respectively, of the bolt and nut sections 7 and 9, respectively, are attached to the rods 3. Such an implanted spinal stabilization system is shown in FIG. 3. Further aspects of the present invention are as follows: the cannulated pedicle bolt 7 accommodates a Kirschner wire ("k-wire") which is used as a pilot locator bolt 7 and is posteriorly inserted over a properly placed k-wire (not shown) through its central aperture and through the pedicle portion of the vertebra to form a posterior portion of a threaded aperture 35; the nut 9 is similarly inserted over the k-wire anteriorly through its central aperture to form an anterior portion of the threaded aperture 35—this aperture 35 is seen best in FIG. 2.

Figure 2:
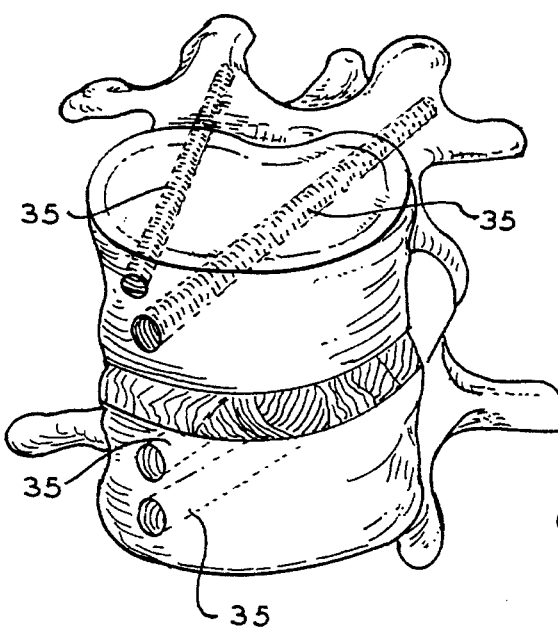
FIG. 2 is a perspective view of two vertebrae and a intervertebral disc showing the threaded apertures which are formed by insertion of two pairs of nut and bolt portions of the present invention.
Figure 5:
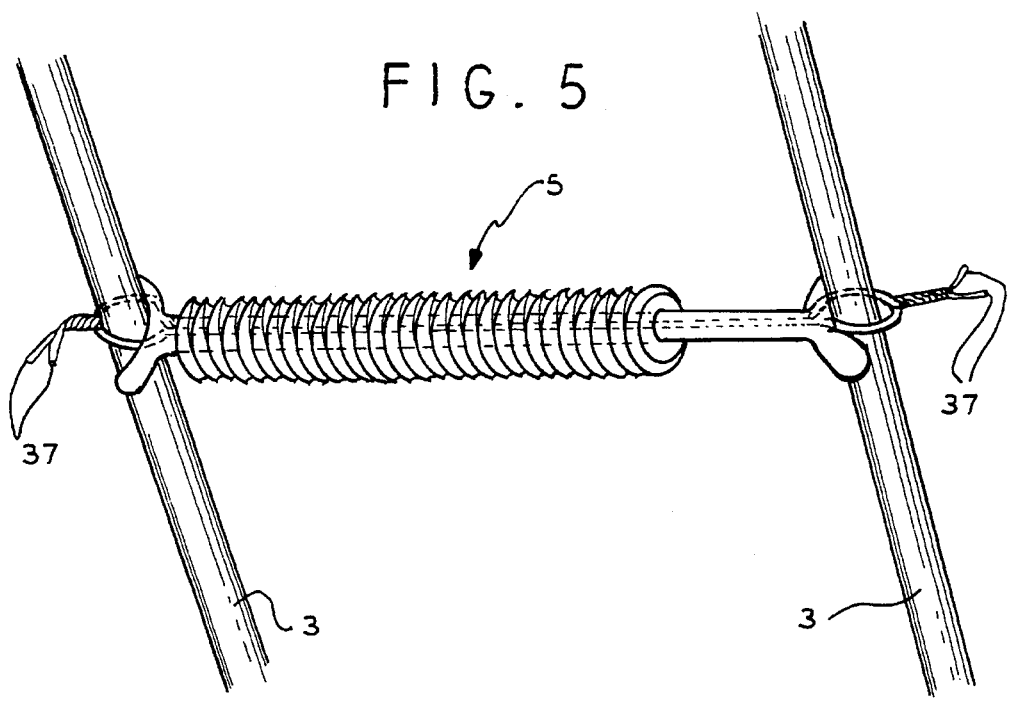
FIG. 5 is a perspective view of a single assembled bolt and nut portions attached at its ends to rods by tie wires.

As seen in FIG. 2 and FIG. 3 the two beam means 5 in an individual vertebra are disposed therein in different planes and form a triangle in cross section through said beam means 5. Also as seen best in FIG. 1, the individual beam means 5 extends through the superior and inferior portions of the same vertebra. The k-wire guide inside the beams means 5 can be replaced with two tie wires 37 which are then twist locked on the rods 3, as seen in FIG. 5, after the beam sections 5 are in place in the vertebrae (not shown in said figure). These twist lock attachments serve to lock the bolt and nut sections 7 and 9, respectively, to the rods 3 to prevent back-off.

The improved surgical technique used for implanting the preferred system of the present invention is essentially the same as the aforedescribed original technique except that the alignment fixture 100 is used in the initial stages of the technique. This improved technique obviates the visual sighting requirement in the original technique which is used to determine the route in the vertebrae.

Figure 7:
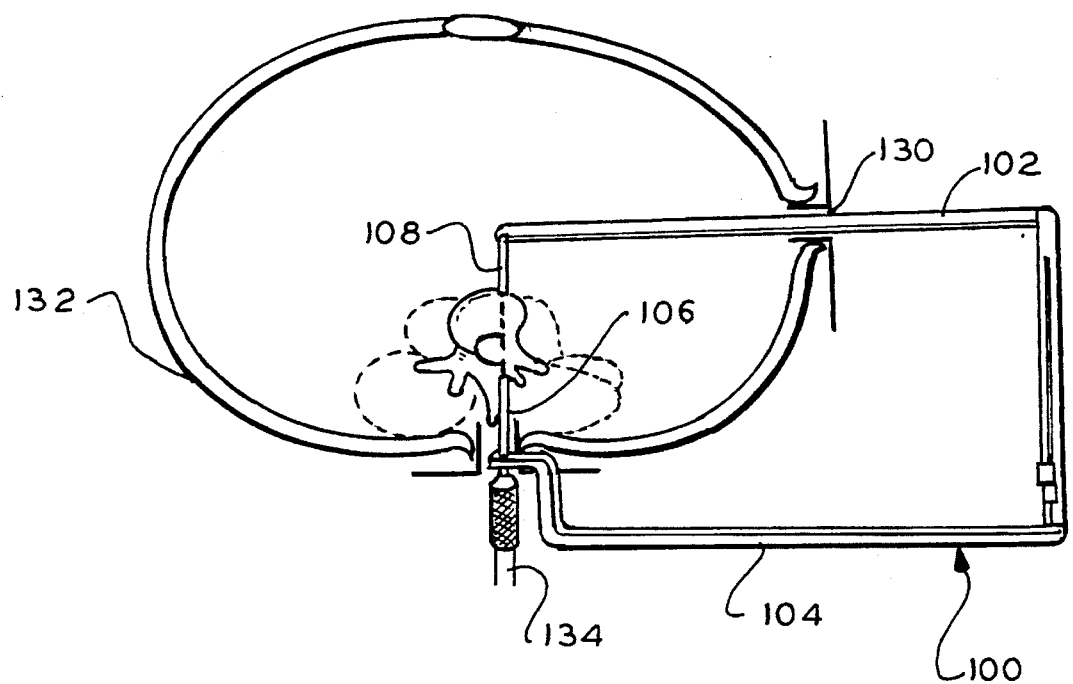
FIG. 7 is a horizontal cross-sectional view of the patient and spine and a side view of the alignment fixture in its installation position adjacent the posterior and anterior aspects of the spine.
Figure 8:
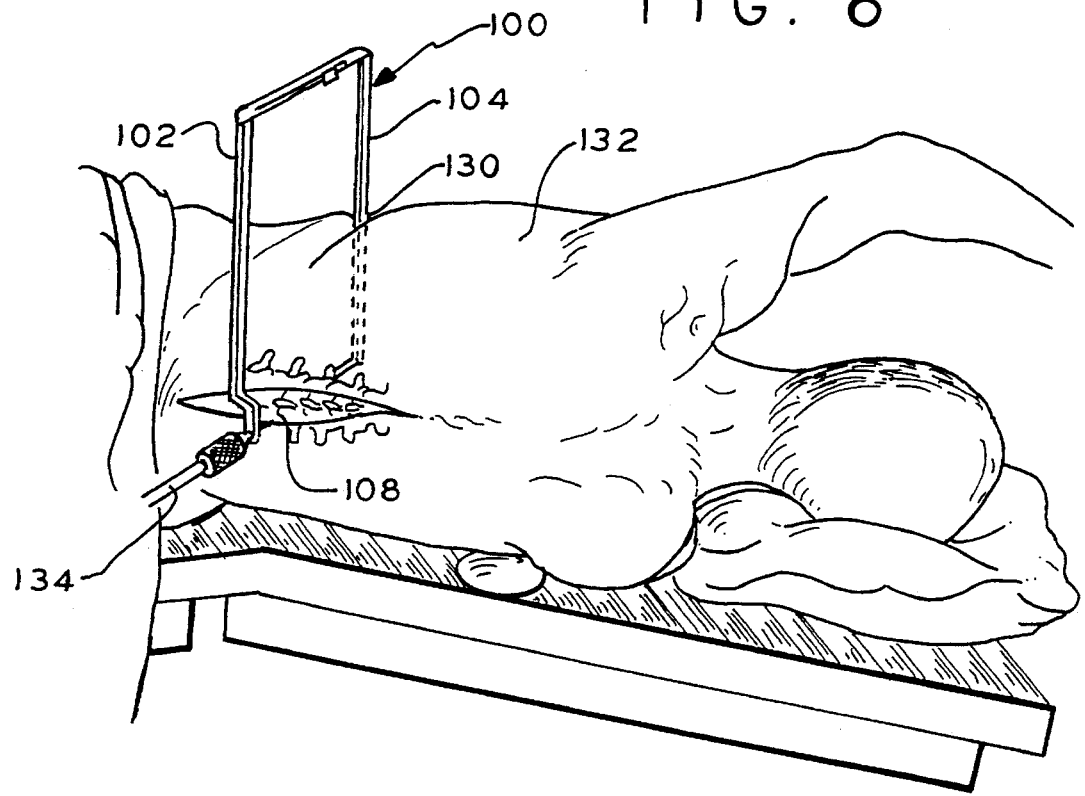
FIG. 8 is a perspective view of the patient with a posterior incision and the alignment fixture positioned in the installation position.

Referring now to FIGS. 7 and 8, the initial stages or steps of the improved technique or process, which occur prior to the installation of the spinal stabilization system 1 are as follows:

a. surgically exposing two adjacent levels of affected vertebrae;

b. cleaning out the contents of pedicle portions of the above affected vertebrae, preferably by curetting, so as to permit sufficient movement of the drill guide means 106 (of the alignment fixture 100) within the cleaned out pedicle portions so that the aiming pin 108 (of the alignment fixture 100) can be (later) positioned at the desired exit points on the anterior aspect of the above affected vertebrae (these exit points conform to the center of the exit opening of aperture 35, as is seen best in FIG. 2);

c. making an incision 130 (FIG. 7) in the lateral aspect of a patient 132 of sufficient size to permit the aiming pin 108 and a portion of its attached arm 102 entry through the incision 130;

d. inserting the aiming pin 108 and a portion of its attached arm 102 through the incision 130 and positioning the aiming pin 108 (by moving first arm 102 inward using the slide) near the anterior aspect of one of the affected vertebrae;

e. inserting the tip of the drill guide means 106 within one of the cleaned out pedicle portions of one affected vertebra (first level);

f. positioning the aiming pin 108 at the desired exit point on the anterior aspect of said one affected vertebrae as is seen best in FIG. 7;

g. inserting the drill bit of a drill 134 (only a portion of which is shown) within the now aligned drill guide means 106 disposed within the pedicle portion of the said one affected vertebra;

h. drilling an aperture into and through the said one affected vertebra, through said drill guide means 106, which emerges at the desired exit point on the anterior aspect of said vertebra;

i. repeating steps e) through h) for the other exit point on the same affected vertebra;

j. inserting a pair of beam means 5 through the same said affected vertebra (first level);

k. repeating steps e) through j) for the second level of affected vertebra;

l. disposing three column means 3 over the anterior and posterior aspects of the two levels of affected vertebrae; and m. connecting the ends 29 and 31 of the beam means 5 at both levels of affected vertebrae to the column means 3.

The nut section 9 has a self-tapping bone screw on its exterior aspects as does the bolt section 7. The bolt section 7 of FIG. 4A preferably has a cutting edge portion 13 around the cannulated opening 11 of 2 mm in length, an externally threaded front portion 17 of greater than between 10 mm to 30 mm in length, an externally threaded middle portion 25 of between 15 mm to 40 mm in length, and a smooth shaft portion 28 of between 20 mm to 40 mm in length. The nut section 9 of FIG. 4A preferably has an externally threaded front portion 19 of about between 10 mm to 30 mm in length, and the aperture 11 thereof has an internal machine thread to meet the machine thread on the tip 13 and front portion 17 of the bolt section 7. The pitch of the matching male and female threads are the same. The preferred materials for the bolt and nut sections 7 and 9, respectively, would be $T_1$-6AI-4V, or a similar material because of its mechanical strength properties and corrosion resistance; other possible materials could be a high strength biodegradable polymer such as a high molecular weight PLA. Stainless steel could even be used.

Although the present invention has been described and illustrated with respect to a preferred embodiment; it is not to be so limited since modifications and changes can be made therein which are within the full intended scope of the invention.

What is claimed is:

1. A spinal stabilization system for fixing vertebrae bodies having anterior and posterior aspects; said system comprising:

a first, a second and a third substantially rigid, elongated column means each being disposed along an anterior aspect or a posterior aspect of said vertebrae bodies, said first column means being disposed along said anterior aspect of said vertebrae bodies and said second column means being disposed along said posterior aspect of said vertebrae bodies; and a plurality of substantially rigid, elongated beam means, each beam means of said plurality of beam means having a longitudinal length for extending through said vertebrae bodies, at least from said anterior aspect to said posterior aspect thereof and, each said beam means having a first end and a second end, said each beam means having a first attachment means at said first end and a second attachment means at said second end said first attachment means for coupling said first end to a column means disposed along said anterior aspect of said vertebrae bodies and said second attachment means for coupling said second end to another column means disposed along said posterior aspect of said vertebrae bodies.

2. The system as recited in claim 1, wherein each of said beam means has an aperture extending along its longitudinal axis.

3. A system as recited in claim 1, wherein each said beam means extends through a same vertebra body of said vertebrae bodies and are disposed therein in different planes.

4. A system as recited in claim 1, wherein a column means of said first, second and third column means is selected from the group consisting of rods and plates and wherein there are three column means.

5. A system as recited in claim 1, wherein said first, second and third column means are aligned along said aspects of said vertebrae bodies so that a cross section of said column means through said beam means forms a triangular configuration.

6. A system as recited in claim 1 wherein said vertebrae bodies have superior and inferior rim portions and wherein each said beam means extends through said superior and inferior rim portions of a same vertebra body of said vertebrae bodies.

7. A system as recited in claim 1, wherein each said beam means comprises a bolt section and a nut section adapted to threadingly engage each other between said anterior aspect and said posterior aspect and within a vertebra body of said vertebrae bodies, said bolt section and said nut section each having a longitudinal axis which join each other when said bolt section and said nut section are threadingly engaged within said vertebra body.

8. A system as recited in claim 7, wherein said bolt section and said nut section each have an aperture extending along respective longitudinal axes thereof.

9. A system as recited in claim 7 wherein said bolt section and said nut section each include a cutting end portion and a front portion having an externally threaded cylindrical periphery with cutting edges, and said nut section includes an aperture having an internally threaded cylindrical periphery for engaging said cutting edges of said externally threaded cylindrical periphery of said front portion of said bolt section.

10. A system as recited in claim 9, wherein said bolt section further includes a middle portion having an externally threaded periphery with cutting edges.

11. A system as recited in claim 9 wherein said bolt section and said nut section further include a rear portion and each said rear portion includes an attachment means for attaching said rear portion of said bolt section and said nut section to said column means.

12. A system as recited in claim 10, wherein a diameter of the cylindrical peripheries of said middle portion of said bolt section and said front portion of said nut section are substantially equal.

13. A system as recited in claim 7 wherein said vertebrae bodies have a pedicle portions and said bolt sections extend through the pedicle portions of said vertebrae body.

14. A system as recited in claim 7 wherein said bolt section and said nut section extend from said posterior aspect and said anterior aspect, respectively, of said vertebra body, and toward each other, and engage each other within said vertebra body.

15. A spinal stabilization system for fixing vertebrae bodies having posterior and anterior aspects, said system comprising:

a plurality of column means being selected from a group consisting of rods and plates;

at least two column means of said plurality of column means being disposed over said vertebrae bodies at least one column means of said at least two column means being disposed over an anterior aspect of said vertebrae bodies and at least another column means of said at least two column means being disposed over a posterior aspect of said vertebrae bodies;

a plurality of beam means, each beam means of said plurality of beam means having a longitudinal length for extending through a vertebra body of said vertebrae bodies and for attaching to a column means of said at least two column means at least two beam means of said plurality of beam means extending through a same vertebra body of said vertebrae bodies and on different planes passing through said same vertebra body; and said each beam means including a bolt section and a nut section each section having a longitudinal axis and an aperture extending along said longitudinal axis each said bolt section and each said nut section including a cutting end portion and a front portion having a cylindrical periphery externally threaded with cutting edges, said aperture of said nut section having a cylindrical periphery internally threaded for engaging said externally threaded cutting edges of said front portion of said bolt section.

16. A spinal stabilization system for fixing vertebrae bodies having anterior and posterior aspects, said system comprising:

a plurality of substantially rigid, elongated column means for being disposed over said vertebrae bodies, at least one column means of said plurality of column means disposed over an anterior aspect of said vertebrae bodies and at least a second column means of said plurality of column means disposed over a posterior aspect of said vertebrae bodies;

a plurality of substantially rigid, elongated beam means, each beam means of said plurality of beam means having a longitudinal length for extending through said vertebrae bodies, said each beam means having first and second ends and first and second attachment means at said first and second ends, respectively, for attaching said beam means to said column means, said each beam means being attached at said first end to a first column means of said plurality of column means which is disposed over said anterior aspect of said vertebrae bodies and said each beam means being attached at said second end to a second column means of said plurality of column means which is disposed over said posterior aspect of said vertebrae bodies;

said each beam means includes a bolt section and a nut section, each having a longitudinal axis which join each other within a vertebra body of said vertebrae bodies, when said bolt section and said nut section are inserted into and through said vertebra body;

said bolt section and said nut section each include a cutting end portion and a front portion having an externally threaded cylindrical periphery, with cutting edges, said nut section including an aperture having an internally threaded cylindrical periphery for engaging said cutting edges of said externally threaded cylindrical periphery of said front portion of said bolt section; and said each beam means includes a longitudinal aperture and a wire means extending through said longitudinal aperture for attaching said beam means to a column means of said plurality of column means.

* * * * *